US012045957B2

(12) United States Patent
Govari et al.

(10) Patent No.: US 12,045,957 B2
(45) Date of Patent: Jul. 23, 2024

(54) VISUALIZING AN ORGAN USING MULTIPLE IMAGING MODALITIES COMBINED AND DISPLAYED IN VIRTUAL REALITY

(71) Applicant: JOHNSON & JOHNSON SURGICAL VISION, INC., Irvine, CA (US)

(72) Inventors: Assaf Govari, Haifa (IL); Vadim Gliner, Haifa (IL)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 139 days.

(21) Appl. No.: 17/475,276

(22) Filed: Sep. 14, 2021

(65) Prior Publication Data
US 2022/0122239 A1     Apr. 21, 2022

Related U.S. Application Data

(60) Provisional application No. 63/094,514, filed on Oct. 21, 2020.

(51) Int. Cl.
*G06T 7/70*     (2017.01)
*A61B 3/12*     (2006.01)
(Continued)

(52) U.S. Cl.
CPC .................. *G06T 5/50* (2013.01); *A61B 3/12* (2013.01); *G02B 27/0172* (2013.01); *G06T 7/70* (2017.01);
(Continued)

(58) Field of Classification Search
CPC ... G06T 5/50; G06T 7/70; G06T 2207/10084; G06T 2207/20212; G06T 2207/30041; G16H 30/20; A61B 3/12; G02B 27/0172
See application file for complete search history.

(56) References Cited

U.S. PATENT DOCUMENTS 4,818,110 A    4/1989 Davidson
5,345,087 A    9/1994 Luber et al.
(Continued)

FOREIGN PATENT DOCUMENTS

CN    109276265 A    1/2019
DE    102013013492 A1    2/2015
(Continued)

OTHER PUBLICATIONS

Draelos M., et al., "Real-time Visualization and Interaction With Static and Live Optical Coherence Tomography Volumes in Immersive Virtual Reality," Biomedical Optics Express, May 2018, vol. 9(6), pp. 2825-2843.
(Continued)

*Primary Examiner* — Shefali D Goradia
(74) *Attorney, Agent, or Firm* — Johnson & Johnson Surgical Vision, Inc.

(57) ABSTRACT

A system including first and second camera assemblies, and a processor. The first camera assembly includes a first camera producing, in a first imaging modality, a first image of an organ acquired from a first angle, and a first position sensor, producing a first position signal indicative of a first position and a first orientation, of the first camera. The second camera assembly includes a second camera, producing, in a second imaging modality, a second image of the organ acquired from a second angle, and a second position sensor, producing a second position signal indicative of a second position and a second orientation, of the second camera. The processor registers between the first and second images based on the first and second position signals and displays, based on the first and second images, a third image including a combination of at least part of the first and second images.

24 Claims, 2 Drawing Sheets

(51) Int. Cl.
*G02B 27/01* (2006.01)
*G06T 5/50* (2006.01)
*G16H 30/20* (2018.01)

(52) U.S. Cl.
CPC ... *G16H 30/20* (2018.01); *G06T 2207/10084* (2013.01); *G06T 2207/20212* (2013.01); *G06T 2207/30041* (2013.01)

(56) References Cited

U.S. PATENT DOCUMENTS

| | | | |
|---|---|---|---|
| 5,391,199 | A | 2/1995 | Ben-Haim |
| 6,006,126 | A * | 12/1999 | Cosman ............... G06V 10/245 600/417 |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 8,049,873 | B2 | 11/2011 | Hauger et al. |
| 8,379,218 | B2 | 2/2013 | Deck et al. |
| 9,844,321 | B1 * | 12/2017 | Ekvall ..................... A61B 90/37 |
| 10,258,426 | B2 | 4/2019 | Silva et al. |
| 10,303,940 | B2 * | 5/2019 | Zhang ..................... G06F 3/011 |
| 10,517,760 | B2 | 12/2019 | Berlin |
| 10,638,080 | B2 | 4/2020 | Ovchinnikov et al. |
| 11,906,745 | B1 | 2/2024 | Zhao et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2004/0106916 | A1 | 6/2004 | Quaid et al. |
| 2004/0257360 | A1 | 12/2004 | Sieckmann |
| 2008/0204864 | A1 | 8/2008 | Sander |
| 2008/0287781 | A1 | 11/2008 | Revie et al. |
| 2009/0278791 | A1 | 11/2009 | Slycke et al. |
| 2013/0293888 | A1 | 11/2013 | Zhao |
| 2014/0160264 | A1 | 6/2014 | Taylor et al. |
| 2014/0179997 | A1 * | 6/2014 | von Grunberg ....... A61B 1/313 600/102 |
| 2014/0296694 | A1 | 10/2014 | Jaworski |
| 2016/0008169 | A1 | 1/2016 | Yu |
| 2016/0183779 | A1 | 6/2016 | Ren et al. |
| 2016/0228204 | A1 | 8/2016 | Quaid et al. |
| 2016/0327806 | A1 | 11/2016 | Kasamatsu |
| 2017/0007450 | A1 | 1/2017 | Samec et al. |
| 2017/0078651 | A1 * | 3/2017 | Russell ................. H04N 13/133 |
| 2017/0280989 | A1 * | 10/2017 | Heeren ................. A61B 34/20 |
| 2018/0008232 | A1 | 1/2018 | Mine et al. |
| 2018/0116728 | A1 | 5/2018 | Lang |
| 2018/0211562 | A1 * | 7/2018 | Rios ........................ A61M 5/48 |
| 2018/0220100 | A1 * | 8/2018 | Ovchinnikov ........ G06F 3/0484 |
| 2018/0220103 | A1 | 8/2018 | Wang et al. |
| 2018/0341323 | A1 | 11/2018 | Mate et al. |
| 2018/0368656 | A1 | 12/2018 | Austin et al. |
| 2019/0000314 | A1 | 1/2019 | Awdeh |
| 2019/0005709 | A1 | 1/2019 | Kim et al. |
| 2019/0101757 | A1 * | 4/2019 | Martinez ............ G02B 27/0172 |
| 2019/0133289 | A1 | 5/2019 | Rocha et al. |
| 2019/0298448 | A1 | 10/2019 | Kerbage et al. |
| 2019/0380566 | A1 | 12/2019 | Charles et al. |
| 2020/0059640 | A1 | 2/2020 | Browd et al. |
| 2020/0069218 | A1 | 3/2020 | Gliner et al. |
| 2020/0107701 | A1 | 4/2020 | Gliner et al. |
| 2020/0188173 | A1 * | 6/2020 | Berlin ..................... A61B 90/20 |
| 2021/0088688 | A1 * | 3/2021 | Chapman ............. G05B 13/048 |
| 2021/0137634 | A1 | 5/2021 | Lang |
| 2021/0186619 | A1 | 6/2021 | Levi et al. |
| 2021/0186620 | A1 | 6/2021 | Gliner et al. |
| 2021/0192759 | A1 | 6/2021 | Lang |
| 2021/0281802 | A1 * | 9/2021 | Kirisken ............... G02B 27/017 |
| 2021/0325649 | A1 * | 10/2021 | Segev ..................... G06F 3/013 |
| 2022/0103744 | A1 | 3/2022 | Hsu et al. |
| 2022/0110691 | A1 | 4/2022 | Govari et al. |
| 2022/0387128 | A1 * | 12/2022 | Bail ........................ A61B 34/74 |
| 2023/0210604 | A1 | 7/2023 | Berman et al. |

FOREIGN PATENT DOCUMENTS

| | | |
|---|---|---|
| EP | 0697611 A2 | 2/1996 |
| EP | 3387984 B1 | 4/2020 |
| WO | 1996005768 A1 | 2/1996 |
| WO | 2017066373 A1 | 4/2017 |
| WO | 2018216156 A1 | 11/2018 |
| WO | 2019148154 A1 | 8/2019 |

OTHER PUBLICATIONS

Draelos, et al., Real-time visualization and interaction with static and live optical coherence tomography volumes in immersive virtual reality, Biomedical Optics Express, May 30, 2018, 2825-2843.

Cho N.H., et al., "In Vivo Imaging Of Middle-Ear and Inner-Ear Microstructures of a Mouse Guided by SD-OCT Combined With A Surgical Microscope," Optics Express, Apr. 21, 2014, vol. 22 (8), pp. 8985-8995, DOI:10.1364/OE.22.008985.

Giorgi C., et al., "Robot-AssistedMicroscope For Neurosurgery," Journal of Image Guided Surgery, 1995, vol. 1 (3), pp. 158-163.

Hussain R., et al., "Video-Based Augmented Reality Combining Ct-Scan And Instrument Position Data To Microscope View In Middle Ear Surgery," Scientific Reports, Nature Research, 2020, vol. 10, pp. 6767, www.nature.com/scientificreports.

* cited by examiner

VISUALIZING AN ORGAN USING MULTIPLE IMAGING MODALITIES COMBINED AND DISPLAYED IN VIRTUAL REALITY

CROSS-REFERENCE TO RELATED APPLICATIONS

This application claims the benefit of U.S. Provisional Patent Application 63/094,514, filed Oct. 21, 2021, whose disclosure is incorporated herein by reference.

FIELD OF THE INVENTION

The present invention relates generally to medical devices, and particularly to methods and systems for visualizing an organ using multiple imaging modalities combined and displayed in virtual reality.

BACKGROUND OF THE INVENTION

During a minimally invasive medical procedure, such as an ophthalmic procedure, a surgeon navigates a medical instrument to a target location within a patient eye. In some cases, a virtual reality image of a region of interest (ROI), may assist the surgeon to plan the ophthalmic procedure. Various techniques have been developed for visualizing ROIs of organs in question using virtual reality techniques.

For example, U.S. Pat. No. 9,844,321 describes an ophthalmic surgical system comprising: a camera optically coupled to a surgical microscope, a virtual reality (VR) headset worn by a surgeon, and a VR data processing unit configured to communicate with the surgical microscope, the VR headset, and an ophthalmic surgical apparatus.

U.S. Pat. No. 10,258,426 describes systems and methods for virtual reality or augmented reality (VR/AR) visualization of 3D medical images using a VR/AR visualization system. The VR/AR visualization system includes a computing device operatively coupled with a VR/AR device, and the VR/AR device includes a holographic display and at least one sensor. The holographic display is configured to display a holographic image to an operator. The computing device is configured to receive at least one stored 3D image of a subject's anatomy and at least one real-time 3D position of at least one surgical instrument. The computing device is further configured to register the at least one real-time 3D position of the at least one surgical instrument to correspond to the at least one 3D image of the subject's anatomy, and to generate the holographic image comprising the at least one real-time position of the at least one surgical instrument overlaid on the at least one 3D image of the subject's anatomy.

SUMMARY OF THE INVENTION

An embodiment of the present invention that is described herein provides a system including first and second camera assemblies, and a processor. The first camera assembly includes (i) a first camera, which is configured to produce, in a first imaging modality, a first image of an organ acquired from a first angle, and (ii) a first position sensor, which is configured to produce a first position signal indicative of at least one of a first position and a first orientation, of the first camera. The second camera assembly includes (i) a second camera, which is configured to produce, in a second imaging modality, a second image of the organ acquired from a second angle, and (ii) a second position sensor, which is configured to produce a second position signal indicative of at least one of a second position and a second orientation, of the second camera. The processor is configured (i) to register between the first and second images based on the first and second position signals and (ii) to display, based on the first and second images, a third image including at least one of: (a) at least part of the first image, (b) at least part of the second image, and (c) a combination of at least part of the first and second images.

In some embodiments, the system includes a display, and at least one of the processor and the display is configured to select one or more display modes of the third image, the display modes are based on one or more of the at least part of the first image, the at least part of the second image, and the combination of the at least part of the first and second images. In other embodiments, the display includes a virtual-reality (VR) head mount display (HMD), which is configured to toggle between the one or more display modes. In yet other embodiments, at least one of the processor and the display is configured to apply a filter to the third image.

In an embodiment, the first and second imaging modalities differ from one another based on one or more parameters selected from the group consisting of: (a) a wavelength or a range of wavelengths, (b) a zoom level, (c) a focal length, (d) a field of view, and (e) a speed. In another embodiment, the processor is configured to adjust one or more of: (i) at least one of the first and second angles, and (ii) at least one of the first and second imaging modalities. In yet another embodiment, the organ includes an eye of a patient, and at least one of the first and second cameras includes a fundus camera.

In some embodiments, the organ includes an eye of the patient, and the system includes a microscope, and at least one of the first and second cameras is coupled with a respective objective of the microscope. In other embodiments, the system includes a first motorized arm configured to move the first camera relative to the organ, and a second motorized arm configured to move the second camera relative to the organ, and the processor is configured to control the first and second motorized arms for adjusting a position of at least one of the first and second cameras relative to the organ. In yet other embodiments, at least one of the first and second camera assemblies includes a filter configured to alter at least one of the first and second images, and the processor is configured to activate the filter for adjusting at least one of the first and second images.

In some embodiments, the system includes a third camera assembly, including (i) a third camera, which is configured to produce, in a third imaging modality, a fourth image of the organ acquired from a third angle, and (ii) a third position sensor, which is configured to produce a third position signal indicative of at least one of: a third position and a third orientation, of the third camera. The processor is configured: (i) to register between the first image, the second image and the fourth image based on the first position signal, the second position signal and the third position signal, and (ii) to display, based on the first image, the second image and the fourth image, a fifth image including an additional combination of at least part of the first image, the second image and the fourth image. In other embodiments, the first imaging modality and the second imaging modality include a same imaging modality or a different imaging modality.

There is additionally provided, in accordance with an embodiment of the present invention, a method including receiving (i) a first image of an organ, the first image is acquired from a first angle using a first camera having a first imaging modality, and (ii) a first position signal indicative of at least one of a first position and a first orientation of the first camera. A second image of the organ is received, the second image is acquired from a second angle using a second camera having a second imaging modality, and a second position signal indicative of at least one of a second position and a second orientation of the second camera, is received. The first and second images are registered based on the first and second position signals. Based on the first and second images, a third image is displayed, the third image including at least one of: (a) at least part of the first image, (b) at least part of the second image, and (c) a combination of at least part of the first and second images.

The present invention will be more fully understood from the following detailed description of the embodiments thereof, taken together with the drawings in which:

DETAILED DESCRIPTION OF EMBODIMENTS

Overview

Figure 1:
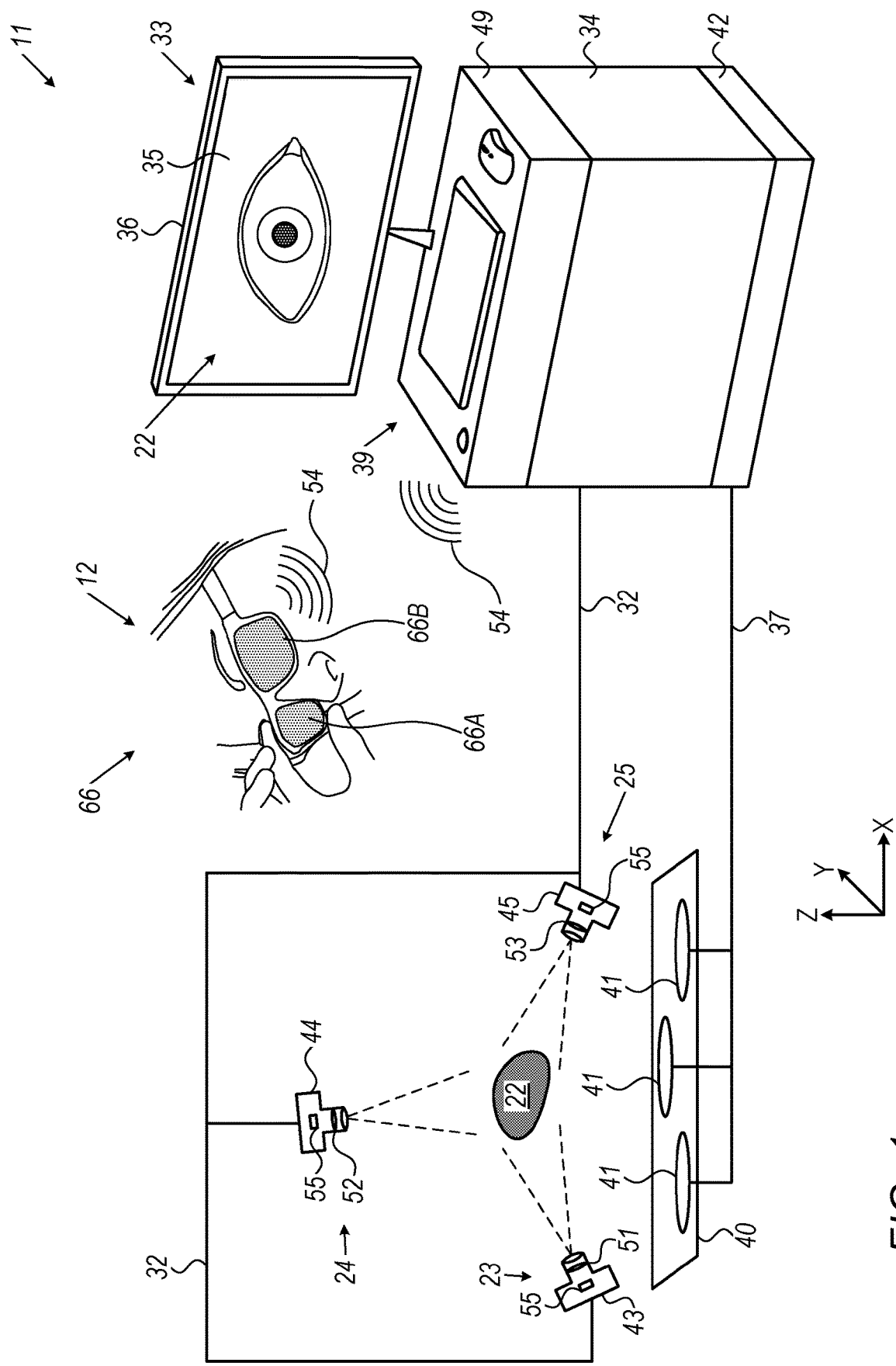
FIG. 1 is a schematic pictorial illustration of an organ visualization system, in accordance with an embodiment of the present invention.

In some medical procedures, a surgeon using an imaging system to examine an organ of a patient may have, during the procedure, to rotate at least part of the imaging system or the patient, so as to view the organ from a different direction. Such rotations are typically not desired during medical procedures.

Embodiments of the present invention that are described hereinbelow provide improved techniques for providing a surgeon with multi-directional images of the organ during a medical procedure, without rotating the imaging system or the patient. Moreover, the disclosed technique provides the surgeon with a capability to combine multiple imaging modalities in one or more of the multi-directional images.

In some embodiments, a multi-directional imaging system, also referred to herein as "a system" for brevity, comprises a plurality of camera assemblies, a position tracking system (PTS), e.g., a magnetic PTS, and a processor. Each camera assembly is movable (e.g., coupled with a controllable motorized arm) relative to an organ in question, so that a surgeon using the system may select a viewing angle of the organ.

In some embodiments, each camera assembly comprises (i) a camera, which is configured to produce, using a given imaging modality, an image of the patient organ acquired from a given angle, and (ii) a position sensor of the PTS, which is typically coupled with the camera and is configured to produce a position signal indicative of the position and orientation of the respective camera. The term imaging modality refers to one or more imaging parameters or attributes, such as but not limited to: a wavelength or a range of wavelengths, a magnification, also referred to herein as a zoom level, and other parameters. At least two of the cameras have imaging modalities different from one another.

In some embodiments, the processor is configured to register between the images received from different cameras. The registration may be carried out based on the position signals received from the position sensors coupled to the respective cameras, and when applicable, using common features that appear in both registered images.

In some embodiments, the processor is configured to display, based on the registered images, a subsequent image comprising a combination of at least two of the registered images. For example, a combination of an optical image (acquired using a visible light-based optical camera) and a thermal image (acquired by an infrared-based camera).

In some embodiments, the system comprises an optical head mount display (HMD) using virtual reality techniques for visualizing the subsequent image comprising the combination of the two or more images.

In some embodiments, in case the cameras of the system cover most of or all the sections of the organ, the processor is configured to display on the HMD a three-dimensional (3D) visualization of the organ. Moreover, in response to an instruction of gaze direction from the surgeon, the processor is configured to virtually rotate the organ and to display selected sections of the organ to the surgeon.

In some embodiments, in response to an instruction from the surgeon, the processor is configured to control the motorized arms for adjusting the angle of at least one of the cameras relative to the organ, so as to obtain a desired combination of imaging modalities used for acquiring images of a section of interest of the organ. For example, in an ophthalmic procedure, each camera may be coupled with a respective objective lens (OL) of an ophthalmic surgical microscope. In such embodiments, the processor is configured to control the position and orientation of the OLs and/or cameras, so as to display on the HMD an image generated by combining images of different imaging modalities produced by the respective cameras.

The disclosed techniques provide the surgeon with a 3D visualization of an organ from different directions using a suitable combination of imaging modalities, without rotating the imaging system or the patient.

System Description

FIG. 1 is a schematic pictorial illustration of an organ visualization system 11, in accordance with an embodiment of the present invention.

In some embodiments, system 11 comprises multiple imaging assemblies, in the present example three camera assemblies 23, 24 and 25, positioned at a different angle relative to an organ in question, e.g., an eye, referred to herein as an organ 22.

In some embodiments, system 11 comprises a magnetic position tracking system (PTS) comprising position sensors 55. In the present example, three position sensors 55 coupled with camera assemblies 23, 24 and 25, respectively, as described in detail herein.

In some embodiments, camera assembly 23 comprises a camera 43, position sensor 55 and an optical filter 51. Camera assembly 24 comprises a camera 44, a position sensor and an optical filter 52, and camera assembly 25 comprises a camera 45, a position sensor 55 and an optical filter 53.

In some embodiments, each camera from among cameras 43-45 is positioned at a different angle relative to organ 22. For example, the angle may be measured relative to one or more axes of an XYZ coordinate system.

Moreover, in some embodiments, at least one of cameras 43-45 may be positioned within the body of a patient (not shown) having organ 22. For example, one of cameras 43-45 may be coupled with a distal end of a medical tool inserted in close proximity to organ 22. Additionally, or alternatively, organ 22 may comprise a patient eye and at least one of cameras 43-45 may comprise miniature cameras, such as a fundus camera, configured to acquire images of the rear of an eye, also known as the fundus.

In some embodiments, the cameras of system 11, e.g., cameras 43-45 and additional cameras (not shown) are distributed around organ 22 so that their images comprise all sections of organ 22, or as much of organ 22 as possible. For large organs the cameras may be stand-alone cameras as shown in FIG. 1.

In other embodiments, e.g., in case organ 22 comprises a small organ, such as an eye, the cameras of system 11 may be attached to a respective objective of a microscope. For example, system 11 may comprise an ophthalmic surgical microscope (not shown) such as but not limited to a stereoscopic microscope (SM). For example, the SM may be selected from the ZEISS OPMI LUMERA series or ZEISS ARTEVO series supplied by Carl Zeiss Meditec AG (Oberkochen, Germany), or any other suitable type of ophthalmic surgical microscope provided by other suppliers.

In some embodiments, cameras of system 11, such as cameras 43-45, may be attached to objectives of the ophthalmic surgical microscope, which is configured to produce stereoscopic images and two-dimensional (2D) optical images of the patient eye. In such embodiments, two or more of cameras 43-45 are coupled with a turret (or to any other suitable assembly of the ophthalmic surgical microscope), and configured to acquire two or more respective optical images of the patient eye from different angles.

In some embodiments, each camera from among cameras 43-45 is configured to produce a different image of organ 22, using a different imaging modality. In the context of the present disclosure and in the claims, the term "imaging modality" refers to one or more imaging parameters or attributes, such as but not limited to: a wavelength or a range of wavelengths, (b) zoom level, (c) focal length, (d) field of view, (e) and speed. Note that in addition to cameras 43-45, or instead of at least one of the cameras, system 11 may comprise additional imaging modalities, such as but not limited to computerized tomography (CT), single-photon emission computed tomography (SPECT), positron emission tomography (PET), and/or any other suitable type of imaging modality.

In some embodiments, camera 43 may comprise a thermographic camera configured to produce thermal images of organ 22 at a range of wavelengths, e.g., at infrared (IR) wavelengths between about 1,000 nm (1 μm) and 14,000 nm (14 μm). In some embodiments, filter 51 of camera assembly 23 is configured to block any wavelength not within the aforementioned range of wavelengths, from being detected by camera 43. In other embodiments, filter 51 is configured to pass a single wavelength within the aforementioned range. Moreover, camera 43 may have an optical magnification between about 1× and 5× (or any other suitable zoom level), and any suitable speed for producing thermal images at suitable rates, e.g., up to about 355 frames per second (fps), having a suitable sensitivity to temperature differences, e.g., as small as about 0.1 centigrade.

In some embodiments, camera 44 may comprise an optical camera configured to produce optical images in the visible light (e.g., in wavelengths between about 400 nm and 750 nm), and having an optical magnification between about 0.5× and 30× (or any other suitable zoom level), and any suitable speed for producing optical images at suitable rates, e.g., up to about 140 fps.

In some embodiments, camera 45 may comprise an optical camera configured to produce optical images in the aforementioned visible light and/or using any other suitable illumination. Camera 45 may have an optical magnification between about 1× and 500× (or any other suitable zoom level), and based on the illumination, camera 45 is configured to visualize various types of materials in organ 22. The materials may comprise foreign materials or materials of the eye, such as residues of the fractured natural lens. Note that when using only the visible light, camera 45 may be configured to produce optical images at higher magnification relative to camera 44.

In some embodiments, camera assemblies 24 and 25 comprise optical filters 52 and 53, respectively, each of which is configured to block one or more selected wavelengths controlled by a surgeon 12 or any other user of system 11. The controllable filtering is also applicable to filter 51 of camera assembly 23 described above.

In some embodiments, system 11 comprises a location pad 40 having a frame and multiple (e.g., three) field-generators 41, each of which is configured to generate a magnetic field at a different frequency. In some embodiments, each position sensor 55 of the aforementioned PTS is configured to generate one or more position signals in response to sensing the external magnetic fields generated by field-generators 41 of location pad 40. In some embodiments, a processor 34 (described in detail below) of system 11 is configured to estimate, based on the position signals, the position and/or orientation of the respective camera assembly in a coordinate system of the PTS.

In some embodiments, each position sensor 55 may comprise a triple-axis sensor (TAS) made from three coils implemented on a printed circuit board (PCB) or using any other suitable technique. Magnetic position sensors are described in further detail, for example in U.S. Pat. Nos. 6,498,944 and 6,690,963, and in U.S. patent Publication No. 2018/0228392, whose disclosures are all incorporated herein by reference.

This method of position sensing is implemented in various medical applications, for example, in the CARTO™ system, produced by Biosense Webster Inc. (Irvine, Calif.) and is further described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication Nos. 2002/0065455 A1, 2003/0120150 A1 and 2004/0068178 A1, whose disclosures are all incorporated herein by reference.

Additionally, or alternatively, the PTS may comprise any other suitable type of PTS, such as but not limited to an optical-based PTS. In such embodiments, at least one position sensor 55 may have a suitable structure other than the coils described above.

In some embodiments, system 11 comprises a console 33, which comprises a memory 49, and a driver circuit 42 configured to drive, via a cable 37, field-generators 41 with suitable signals so as to generate the magnetic fields in a predefined working volume, such as in suitable any region of interest surrounding organ 22.

In some embodiments, console 33 comprises processor 34, typically a general-purpose computer, with suitable front end and interface circuits for receiving the position signals from position sensors 55 coupled with respective camera assemblies 23-25. In the present example, processor 34 receives the position signals via a cable 32; and may use cable 32 for exchanging any suitable signals with other components of system 11. Other means of transmitting and receiving signals known in the art are also contemplated, e.g. BLUETOOTH or other wireless connection. Console 33 further comprises input devices 39 and a display 36 (which may also be, for example, a keyboard, touch screen graphical user interface, or the like).

In some embodiments, processor 34 is configured to receive the aforementioned images from camera assemblies 23-25, via cable 32 (although other means of transmitting and receiving signals known in the art may be used). Based on the position signals received from position sensors 55, processor 34 is configured to register between the received images.

In some embodiments, based on the received optical and/or thermal images, processor 34 is configured to display an optical image 35 on display 36 and/or on an optical head mount display (HMD) 66 described herein. Note that the image(s) displayed on HMD 66 and/or on display 36, may comprise a combination of the thermal and/or optical images received from camera assemblies 23-25.

In some embodiments, processor 34 is configured to display in image 35 one or more of the following: (i) a stereoscopic image by using two or more separate images received from two or more of camera assemblies 23-25; (ii) a 2D optical image, e.g., by using an image received from one selected camera assembly from among camera assemblies 23-25 of system 11; (iii) a thermal image, e.g., by using an image received from one selected camera assembly from among camera assemblies 23-25 of system 11; and/or (iv) any other suitable type of a 2D image and/or a 3D image that processor 34 is configured to combine and/or display. For example, in such procedure planning applications and/or during medical procedures, surgeon 12 may control processor 34 to display the stereoscopic image on HMD 66 and one or more of the 2D images on display 36.

In some embodiments, system 11 comprises HMD 66 using virtual reality techniques for visualizing at least one of the optical images generated by one or more of camera assemblies 23-25. In the context of the present disclosure and in the claims, the terms HMD and virtual reality HMD (VRHMD) are used interchangeably and refer to HMD 66. In some embodiments, HMD 66 comprises a first display 66A mounted in front of a first eye (e.g., right eye) of surgeon 12, and a second display 66B mounted in front of a second eye (e.g., left eye) of surgeon 12. Displays 66A and 66B are configured to display, respectively, to the right and left eyes of surgeon 12, images received from processor 34.

In other embodiments, HMD 66 may comprise an augmented reality HMD (ARHMD). In such embodiments, processor 34 is configured to register between the image displayed on the ARHMD and the patient eye, so as to overlay the displayed image on the patient eye.

In some embodiments, HMD 66 and console 33 have wireless devices (not shown) configured to exchange wireless signals 54 for transferring, inter alia, the aforementioned 2D and/or stereoscopic image.

In some embodiments, because the images were acquired using multiple imaging modalities of camera assemblies 23-25 (which may be different or the same), processor 34 is configured to register between the images based on the position signals received from position sensors 55, and where applicable, processor 34 may also register between the images based on common features that appear in two or more of the received images. Moreover, the registration between the different types of images may be carried out based on a calibration between the different cameras (e.g., performed before the medical procedure) using a calibration jig (not shown).

For example, processor 34 may receive, e.g., from camera assemblies 24 and 25 first and second optical images of respective different sections of organ 22, acquired at different optical magnifications. Therefore, such images may not have common features essential to carry out image-based registration. In such embodiments, processor 34 is configured to register between the first and second images, based on the position signals received from position sensors 55 of camera assemblies 24 and 25.

Similarly, processor 34 may receive, e.g., from camera assemblies 23 and 25, a first image, e.g. a thermal image, of a first section of organ 22 and a second image, e.g., an optical image, of a second section of organ 22, respectively. Even if the first and second sections have some overlap with one another, the different type of imaging modalities may not provide processor 34 with sufficient features for registering between the thermal and optical images. Thus, processor 34 may rely on a combination of: (i) the position signals received from position sensors 55 of camera assemblies 23 and 25, and (ii) the magnification used in cameras 43 and 45, for registering between the thermal and optical images.

In some embodiments, processor 34 is configured to generate, based on the first and second images, a third image, which is based on a combination of the first (e.g. thermal) and second (e.g. optical) images received from camera assemblies 23 and 24 and registered based on at least the position signals as described above.

In such embodiments, processor 34 is configured to display, e.g., on HMD 66, a visualization of multiple sections of organ 22, wherein one or more of the images of the sections of organ 22 comprise a combination of images acquired using multiple (which may be different or the same) imaging modalities. In some embodiments, all camera assemblies 23-25 may have the same imaging modality acquiring the images from different angles. In such embodiments, processor 34 is configured to display on HMD 66, a visualization of multiple sections of organ 22 comprising a combination of the images acquired using the same imaging modality.

In some embodiments, in case surgeon 12 is interested in visualizing a particular section of organ 22 that requires multiple images acquired using different imaging modalities (e.g., thermal and optical images), processor 34 is configured to control motorized arms (not shown), which are coupled with camera assemblies 23-25, so as to acquire images of the particular section. Processor 34 is further configured to display (e.g., on HMD 66) a combined image (e.g. one or more optical or thermal images) of the particular section of interest for surgeon 12. In such embodiments, processor 34 is configured to control the motorized arms for controlling the movement of one or more of the aforementioned camera assemblies, based on the imaging modality (e.g., zoom level and field of view) and the position signals of the respective camera assemblies.

In some embodiments, surgeon 12 can select the gaze direction for displaying the visualization of organ 22, for example, by using a pointing device such as a mouse or a trackball of input devices 39, or using a virtual reality technique implemented in HMD 66. For example, in case cameras 43-45 of system 11 cover most of or all the sections of organ 22, processor 34 is configured to display on HMD 66 a three-dimensional (3D) visualization of organ 22. Moreover, processor 34 is configured to virtually rotate organ 22 and display selected sections in response to the aforementioned selection of gaze direction by surgeon 12.

Additionally, or alternatively, HMD 66 may have control buttons (not shown) embedded in the HMD frame that surgeon 12 may use (e.g., using his/her fingers as shown in FIG. 1) for controlling the image displayed by processor 34. For example, surgeon 12 may use the buttons to: (i) add or remove an image acquired by one of cameras 43-45 from the virtual reality image displayed on HMD 66, and/or (ii) enable or disable at least one of filters 51-53 that may affect the virtual reality image displayed on HMD 66.

In some embodiments, in response to instructions from surgeon 12, processor 34 is configured to display a customized visualization of a selected section of organ 22. For example, processor 34 may store in memory 49, for a selected section of organ 22, an IR-based thermal image acquired by camera 43, and an optical image acquired by camera 44. In response to an instruction received from surgeon 12, processor 34 is configured to: (i) apply optical filter 53 to an image of the selected section that is acquired by camera 45, and (ii) produce a subsequent image comprising a combination of the filtered image acquired by camera 45, with the IR-based thermal image from camera 43 and the optical image from camera 44 as described above. Such combined image may provide surgeon 12 with a complementary information of the selected section of organ 12.

In other embodiments, processor 34 is configured to display an image comprising at least part (e.g., a section or an unfiltered wavelength) of a first (e.g., thermal) image acquired by a first camera (e.g., camera 43) combined with at least part (e.g., a section or an unfiltered wavelength) of a second image acquired by a second camera (e.g., camera 45). For example, in case of particles (e.g., foreign particles or residues of the fractured natural lens) located at a section of organ 22, processor 34 is configured to display a filtered image of the respective section that are acquired by camera 45, and a thermal image of a peripheral section surrounding the particles, which is acquired by camera 43. Based on this combined image, surgeon 12 can examine both the particles, which are emphasized by the filtered image acquired by camera 45, and the temperature distribution in the section surrounding the particles.

In some embodiments, processor 34 is configured to display, to surgeon 12 or to any other user of HMD 66 having a gaze on a scene (e.g., organ 22 of the patient, or display 36), stereoscopic images that are made of one or more of the aforementioned thermal and/or optical images overlaid on one another.

In alternative embodiments, HMD 66 may comprise a processor (not shown), which is configured to carry out at least some of the operations carried out by processor 34 and described above. In such embodiments, at least some of the images described above may be transmitted directly (wirelessly or via cables) to the processor of HMD 66, which may generate and display the one or more virtual reality images on HMD 66.

This particular configuration of system 11 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of imaging systems used in conjunction with or as imaging modules of ophthalmic and other sort of surgical systems.

Figure 2:
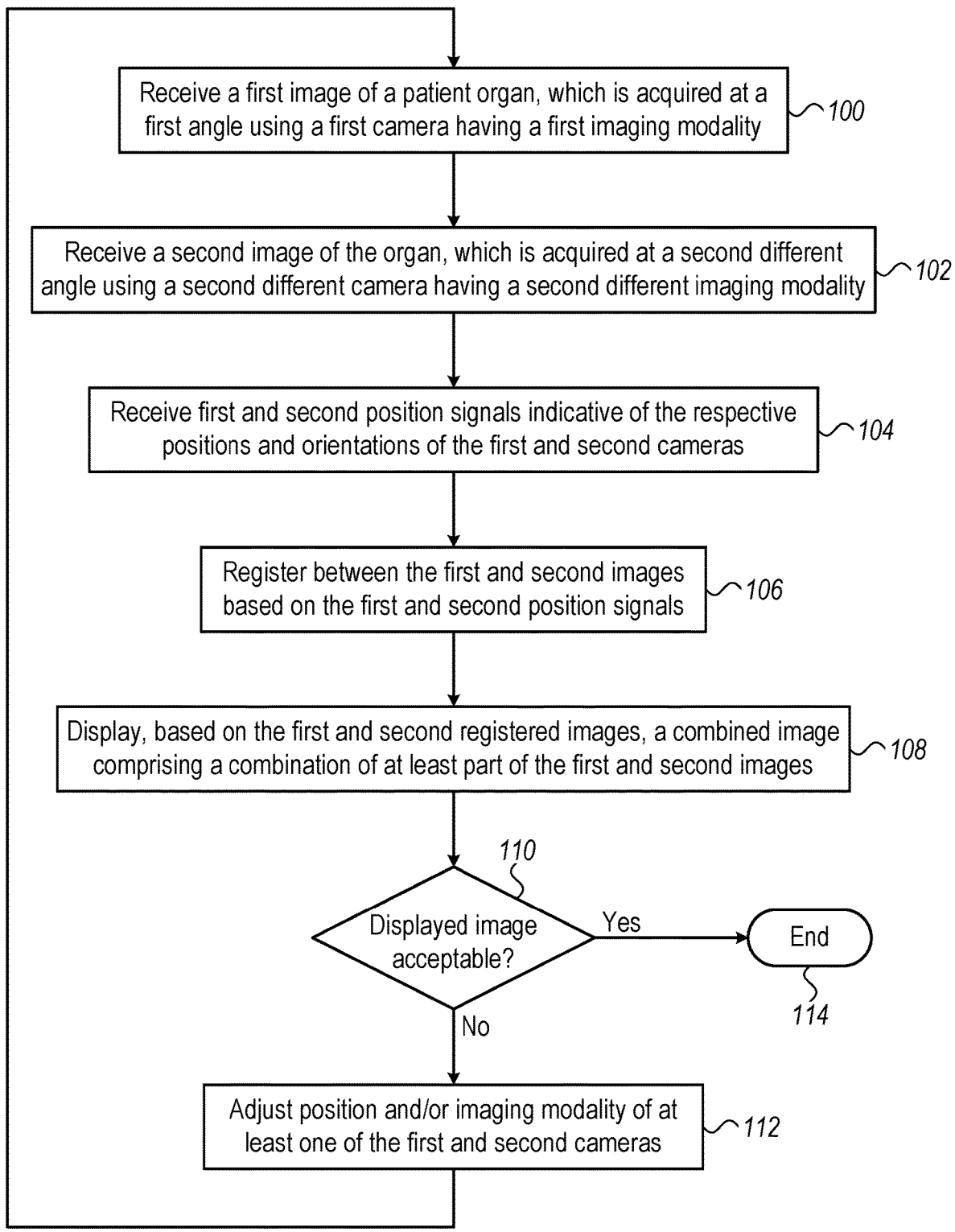
FIG. 2 is a flow chart that schematically illustrates a method for visualizing an organ using multiple imaging modalities combined and displayed in virtual reality, in accordance with an embodiment of the present invention.

Visualizing an Organ Using Multiple Imaging Modalities Combined and Displayed in Virtual Reality FIG. 2 is a flow chart that schematically illustrates a method for visualizing organ 22 using multiple imaging modalities combined and displayed in virtual reality, in accordance with an embodiment of the present invention.

The method begins at a first image receiving step 100 with processor 34 receiving a first image (e.g., a thermal image) of patient organ 22, which is acquired at a first angle using a first camera (e.g., camera 43) having a first imaging modality described in detail in FIG. 1 above.

At a second image receiving step 102 processor 34 receives a second image (e.g., an optical image) of patient organ 22, which is acquired at a second angle using a second camera (e.g., camera 44) having a second imaging modality. In some embodiments, cameras 43 and 44 are configured to acquire the first and second images using the same imaging modality or different imaging modalities. In other embodiments, processor 34 is configured to move a single camera (e.g., camera 43) so as to acquire two images from two different angles. In yet other embodiments, processor 34 is configured to receive three images acquired by cameras 43, 44 and 45 using the same or different imaging modalities.

In alternative embodiments, processor 43 receives, in addition to or instead of at least one of the three images, a different type of one or more images acquired using a different type of imaging modality technique (e.g., a CT image, and/or a SPECT image, and/or a PET image described in FIG. 1 above).

At a position signals receiving step 104, processor 34 receives from position sensors 55, first and second position signals indicative of the position and orientation of the first and second cameras, respectively. In some embodiments, processor 34 receives from position sensor 55 of camera assembly 25 a third position signal indicative of the position and orientation of the third camera (e.g., camera 45).

At a registration step 106, processor 34 registers between the first and second images based on the first and second position signals. In some embodiments, processor 34 may use additional elements for the registration, such as information of the imaging modality (e.g., zoom level applied to each camera), common features that appear at the first and second images (which may use as registration anchors), and a calibration between the different cameras and/or other imaging tools, which is typically carried out before the medical procedure, using a calibration jig as described in FIG. 1 above. In other embodiments, processor 34 registers between the three received images based on the first, second and third position signals described above.

At an image displaying step 108, based on the first and second registered images, processor 34 displays, e.g., on HMD 66, a combined image comprising a combination of at least part of the first and second images. In other embodiments, processor 34 displays on HMD 66 a combined image comprising a combination of at least part of the three received images described above. In the context of the present disclosure and in the claims, the term "at least part of the first and second images" refers to a section of or a filtered image of at least one of the first and second images, as described in detail in FIG. 1 above.

At a decision step 110, surgeon 12 decides whether or not the combined image is sufficient for planning or performing the medical procedure. In case the combined image is not acceptable by surgeon 12, the method proceeds to an adjustment step 112, with processor 34 adjusting the position and/or orientation, of the first camera, the second camera, and/or the third camera relative to organ 22; and/or adjusting the imaging modality of the first camera, the second camera, and/or the third camera, and subsequently, the method loops back to step 100.

In case surgeon 12 is satisfied with the combined image, the imaging method is terminated with the combined image displayed on HMD 66 and/or display 35, and subsequently, surgeon 12 may select to display an additional section of organ 22 and reactivates the method described above on the newly selected section.

Although the embodiments described herein mainly address imaging of patient organs using different imaging modes and applying virtual reality techniques, the methods and systems described herein can also be used in other applications, such as in spine surgery, and in orthopedic procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
    a first camera assembly, comprising
        (i) a first camera, which is configured to produce, in a first imaging modality, a first image of an organ acquired from a first angle, and
        (ii) a first magnetic position sensor, located on the first camera, and which is configured to produce a first position signal indicative of at least one of: a first position and a first orientation, of the first camera;
    a second camera assembly, comprising
        (i) a second camera, which is configured to produce, in a second imaging modality, a second image of the organ acquired from a second angle, and
        (ii) a second magnetic position sensor, located on the second camera, and which is configured to produce a second position signal indicative of at least one of: a second position and a second orientation, of the second camera; and
    a processor, which is configured
        (i) to register between the first image and the second image based on the first and second position signals and
        (ii) to display, based on the first image and the second image, a third image comprising at least one of: (a) at least part of the first image, (b) at least part of the second image, and (c) a combination of at least part of the first image and the second image.

2. The system according to claim 1, further comprising a display, wherein at least one of the processor and the display is configured to select one or more display modes of the third image, wherein the display modes are based on one or more of the at least part of the first image, the at least part of the second image, and the combination of the at least part of the first and the second images.

3. The system according to claim 2, wherein the display comprises a virtual-reality (VR) head mount display (HIVID), which is configured to toggle between the one or more display modes.

4. The system according to claim 2, wherein at least one of the processor and the display is configured to apply a filter to the third image.

5. The system according to claim 1, wherein the first imaging modality and second imaging modality differ from one another based on one or more parameters selected from the group consisting of: (a) a wavelength or a range of wavelengths, (b) a zoom level, (c) a focal length, (d) a field of view, and (e) a speed.

6. The system according to claim 1, wherein the processor is configured to adjust one or more of: (i) at least one of the first angle and the second angle, and (ii) at least one of the first imaging modality and the second imaging modality.

7. The system according to claim 1, wherein the organ comprises an eye of a patient, and wherein at least one of the first camera and the second camera comprises a fundus camera.

8. The system according to claim 1, wherein the organ comprises an eye of a patient, and further comprising a microscope, and wherein at least one of the first camera and second camera is coupled with a respective objective of the microscope.

9. The system according to claim 1, further comprising a first motorized arm configured to move the first camera relative to the organ, and a second motorized arm configured to move the second camera relative to the organ, and wherein the processor is configured to control at least one of the first motorized arm and the second motorized arm for adjusting a position of at least one of the first camera and the second camera relative to the organ.

10. The system according to claim 1, wherein at least one of the first camera assembly and the second camera assembly comprises a filter configured to alter at least one of the first image and the second image, and wherein the processor is configured to apply the filter for adjusting at least one of the first image and the second image.

11. The system according to claim 1, further comprising a third camera assembly, comprising (i) a third camera, which is configured to produce, in a third imaging modality, a fourth image of the organ acquired from a third angle, and (ii) a third magnetic position sensor, which is configured to produce a third position signal indicative of at least one of: a third position and a third orientation, of the third camera, and wherein the processor is configured to: (i) register between the first image, the second image and the fourth image based on the first position signal, the second position signal and the third position signal and (ii) display, based on the first image, the second image and the fourth image, a fifth image comprising an additional combination of at least part of the first image, the second image and the fourth image.

12. The system according to claim 1, wherein the first imaging modality and the second imaging modality comprise a same imaging modality or a different imaging modality.

13. A method, comprising:
    receiving (i) a first image of an organ, wherein the first image is acquired from a first angle using a first camera having a first imaging modality, and (ii) a first magnetic field-based position signal from a first magnetic sensor located on the first camera, indicative of at least one of a first position and a first orientation of the first camera;
    receiving (i) a second image of the organ, wherein the second image is acquired from a second angle using a second camera having a second imaging modality, and (ii) a second magnetic field based position signal from a second magnetic sensor located on the second camera, indicative of at least one of a second position and a second orientation of the second camera;

registering between the first image and the second image based on the first position signal and the second position signal; and displaying, based on the first image and the second image, a third image comprising at least one of: (a) at least part of the first image, (b) at least part of the second image, and (c) a combination of at least part of the first image and the second image.

14. The method according to claim 13, further comprising selecting one or more display modes of the third image, wherein the display modes are based on the at least part of the first image, the at least part of the second image, and the combination of the at least part of the first image and the second image.

15. The method according to claim 14, wherein displaying the third image comprises toggling between the display modes using a virtual-reality (VR) head mount display (HMD).

16. The method according to claim 14, wherein displaying the third image comprises applying a filter to the third image.

17. The method according to claim 13, wherein the first imaging modality and the second imaging modality differ from one another based on one or more parameters selected from the group consisting of: (a) a wavelength or a range of wavelengths, (b) a zoom level, (c) a focal length, (d) a field of view, and (e) a speed.

18. The method according to claim 13, further comprising, adjusting one or more of:
(i) at least one of the first angles and the second angle, and
(ii) at least one of the first imaging modality and the second imaging modality.

19. The method according to claim 13, wherein the organ comprises an eye of a patient, and wherein at least one of the first camera and the second camera comprises a fundus camera.

20. The method according to claim 13, wherein the organ comprises an eye of a patient, and wherein at least one of the first image and the second image is received from at least one of the first camera and the second camera, which is coupled with a respective objective of a microscope.

21. The method according to claim 13, further comprising adjusting a position of at least one of the first camera and the second camera relative to the organ.

22. The method according to claim 13, further comprising adjusting at least one of the first image and the second image by applying, to at least one of the first camera and the second camera, a filter for altering at least one of the first image and the second image.

23. The method according to claim 13, further comprising receiving (i) a fourth image of the organ, wherein the fourth image is acquired from a third angle using a third camera having a third imaging modality, and (ii) a third magnetic field based position signal indicative of at least one of a third position and a third orientation of the third camera, wherein registering comprises registering between the first image, the second image, and the fourth image based on the first position signal, the second position signal and the third position signal, and wherein displaying comprises displaying, based on the first image, the second image and the fourth image, a fifth image comprising a combination of at least part of the first image, the second image and the fourth image.

24. The method according to claim 13, wherein the first imaging modality and the second imaging modality comprise a same imaging modality or a different imaging modality.

* * * * *